(12) United States Patent
Dordick et al.

(10) Patent No.: US 7,202,030 B2
(45) Date of Patent: Apr. 10, 2007

(54) SOLID-PHASE ARRAY-BASED BIOCATALYTIC TRANSFORMATIONS

(75) Inventors: Jonathan S. Dordick, Schenectady, NY (US); Lakshmi Santhanam, Troy, NY (US); Michael G. Hogg, Delmar, NY (US); James A. Holland, Voorheesville, NY (US)

(73) Assignees: Rensselaer Polytechnic Institute, Troy, NY (US); The United States of America as represented by the Secretary, Department of Veterans Affairs, Washington, DC (US)

( * ) Notice: Subject to any disclaimer, the term of this patent is extended or adjusted under 35 U.S.C. 154(b) by 504 days.

(21) Appl. No.: 10/287,434

(22) Filed: Nov. 1, 2002

(65) Prior Publication Data

US 2003/0166177 A1 Sep. 4, 2003

Related U.S. Application Data

(60) Provisional application No. 60/334,617, filed on Nov. 1, 2001.

(51) Int. Cl.
*C12Q 1/68* (2006.01)
*C40B 40/14* (2006.01)

(52) U.S. Cl. .......................................................... 435/6
(58) Field of Classification Search ...................... None
See application file for complete search history.

(56) References Cited

U.S. PATENT DOCUMENTS

| | | | |
|---|---|---|---|
| 5,902,831 | A | 5/1999 | Holland et al. |
| 5,919,523 | A | 7/1999 | Sundberg et al. |
| 6,025,371 | A | 2/2000 | Gordeev et al. |
| 6,090,912 | A | 7/2000 | Lebl et al. |
| 6,251,689 | B1 | 6/2001 | Laborde et al. |
| 6,274,383 | B1 | 8/2001 | Gao |
| 2001/0017269 | A1 | 8/2001 | Heller et al. |
| 2002/0185184 | A1 | 12/2002 | O'Connor et al. |

FOREIGN PATENT DOCUMENTS

WO WO 9525737 * 10/1995

OTHER PUBLICATIONS

Iwahara, K.; Honda, Y.; Watanabe, T.; Kuwahara, M. "Polymerization of guaiacol by lignin-degrading manganese peroxidase from Bjerkandera adusta in aqueous organic solvents" Appl. Microbiol. Biotechnol. Jul. 2000, 54, 104-111.*

Suckau, D.; Koster, C.; Hufnagel, P.; Drauter, K.-O.; Rapp, U. "Automation of MALDI-TOF Analysis for Proteomics" Application Note #MT-50. 1999, 1-5.*

Alam et al. "DNA-Binding Peptides Search from the Solid-Phase Combinatorial Library with the Use of the Magnetic Beads Attaching the Target Duplex DNA" Bioorganic & Medicinal Chemistry 2000, 8, 465-473.*

Wu, et al. "Enzymatically and Combinatorially Generated Array-Based Polyphenol Metal Ion Sensor" Biotechnol. Prog. 2000, 16, 513-516 US-.*

Solomons, T. W. G. Organic Chemistry Fifth Edition. New York: John Wiley and Sons. 1992, pp. 942 and 943.*

Heistand II et al. "Catecholate and Phenolate Iron Complexes as Models for the Dioxygenases" J. Am. Chem. Soc. 1982, 104, 2789-2796.*

Haswell, S.J., et al., "Chemical and Biochemical Microreactors," *Trends in Analytical Chemistry*, 19(6): 389-395 (2000).

Drott, J., et al., "Porous silicon as the carrier matrix in microstructured enzyme reactors yielding high enzyme activities," *J. Micromech. Microeng.*, 7: 14-23 (1997).

Laurell, T., et al., "Silicon wafer integrated enzyme reactors," *Biosensors & Bioelectronics*, 10: 289-299 (1995).

Nagy, G., et al., "Amperometric Microcell for Enzyme Activity Measurements," *Analytical Chemistry*, 70(10):2156-2162 (1998).

* cited by examiner

*Primary Examiner*—Jon Epperson
(74) *Attorney, Agent, or Firm*—Hamilton, Brook, Smith & Reynolds, P.C.

(57) ABSTRACT

This invention relates to the enzymatic synthesis of oligophenols on solid support by sequential enzymatic addition of reaction solutions containing phenols. The oligomers are then selectively built up on the solid surface. When used in a specific format, the oligomers can be generated in a spatially addressable array, which can then be screened for some type of biological interaction. The synthetic compounds of the present invention are synthesized in a combinatorial manner on solid support using peroxidase or other related enzymatic catalysis, and the products are generated in spatially addressable microarrays. Oligophenols of the present invention have shown significance as potential inhibitors of NADPH oxidase assembly, an enzyme that has been implicated in a wide range of diseases stemming from vascular hyperpermeability.

12 Claims, 9 Drawing Sheets

FIG. 4C

SOLID-PHASE ARRAY-BASED BIOCATALYTIC TRANSFORMATIONS

RELATED APPLICATION(S)

This application claims the benefit of U.S. Provisional Application No. 60/334, 617, filed Nov. 1, 2001.

The entire teachings of the above application are incorporated herein by reference.

GOVERNMENT SUPPORT

The invention was supported, in whole or in part, by a grant from Department of Veterans Affairs. The Government has certain rights in the invention.

BACKGROUND OF THE INVENTION

Drug discovery often involves assays, that determine the activity of potential drug candidate against specific biological materials, including cells, cellular components, and biomimetic analogs. Such assays are often performed in the presence of a panel of molecules. Where an assayed molecule modulates these specific biological or biomimetic materials in a desirable fashion, this molecule can then undergo further, more specific testing for use as a pharmaceutical preparation or can be chemically or biologically modified to augment its activity. The modified molecule that exhibits the best profile of beneficial activity is then formulated as a drug for the treatment of the targeted pathological process.

One can assay the activity of tens of thousands of molecules simultaneously when using high-throughput screening (HTS) techniques. Where molecules can only be synthesized one at a time, the rate of molecule submission to an assay becomes a debilitating, limiting factor. This problem has led researchers to develop methods by which large numbers of molecules possessing diverse chemical structures can be rapidly and efficiently synthesized. One such method is the construction of chemical combinatorial libraries.

Chemical combinatorial libraries are diverse collections of molecular compounds. Gordon et al. (1995) *Acc. Chem. Res.* 29:144–154. These compounds are formed using a multistep synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

The initial work in combinatorial library construction focused on peptide synthesis. Furka et al. (1991) *Int. J Peptide Protein Res.* 37:487–493; Houghton et al. (1985) *Proc. Natl. Acad. Sci. USA* 82:5131–5135; Geysen et al. (1984) *Proc. Natl. Acad. Sci. USA* 81:3998–4002; and Fodor et al. (1991) *Science* 251:767.

Polycarbamate and N-substituted glycine libraries have been synthesized containing chemical entities that are similar to peptides in structure, but possess enhanced proteolytic stability, absorption and pharmacokinetic properties. Cho et al. (1993) *Science* 261:1303–1305; Simon et al. (1992) *Proc. Natl. Acad. Sci. USA* 89:9367–9371. Furthermore, benzodiazepine, pyrrolidine, and diketopiperazine libraries have been synthesized. Bunin et al. (1992) *J. Am. Chem. Soc.* 114:10997–10998; Murphy et al. (1995) *J. Am. Chem. Soc.* 117:7029–7030; and Gordon et al. (1995) *Biorg. Medicinal Chem. Lett.* 5:47–50. Oligosaccharides have also been synthesized on solid support. P. H. Seeberger, S. J. Danishefsky, *Acc. Chem. Res.*, 31 (1998), 685. However, a need exists to develop new combinatorial libraries, particularly those that are difficult to prepare using traditional synthetic chemistry.

SUMMARY OF THE INVENTION

The present invention relates to step-wise enzymatic synthesis of combinatorial libraries of polymeric compounds and methods for manufacture and uses thereof. More particularly, such libraries are prepared on solid support and thereby provide an addressable array of complex polymer structures. The combinatorial libraries synthesized according to the present invention can be employed in a variety of ways, including, but not limited to (a) identification of drugs or clinical candidates; (b) identification of therapeutically important targets; (c) identification of pharmacophores; (d) identification of active sites of therapeutical targets; (e) identification of markers in cellular signaling, recognition and adhesion; and (f) detection of antibody epitopes.

The present invention provides compositions and methods for generating and screening libraries of phenolic/anilinic polymers (and their related quinone forms) exemplified in one embodiment by the oligophenols and in another embodiment by quinone, said polymers addressably attached to a suitable surface and synthesized using enzymatic catalysis. Thus the present invention provides a method that is useful for generating easily manipulatable libraries of biologically active molecules in a configuration suitable for the high-throughput screening for use in drug discovery and related fields.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The FIG. 1 is a schematic diagram of high-throughput enzymatic synthesis and screening of an oligophenol library.

The FIG. 2A shows an embodiment of the chemical process of functionalizing the solid support to provide chemical groups as synthesis initiation sites.

The FIG. 2B shows an embodiment of the chemical process of functionalizing the solid support to provide chemical groups as synthesis initiation sites using bifunctional linker molecule.

The FIGS. 3A, 3B, and 3C show the monitoring of a successful soybean peroxidase mediated phenol-phenol coupling on a glass slide by quantifying the density of reactive amino groups. In particular, tyramine has been successfully attached to the seed phenol.

DETAILED DESCRIPTION OF THE INVENTION

A description of preferred embodiments of the invention follows.

The instant invention relates to combinatorial libraries of synthetic compounds addressably attached to a solid support and methods of generating the libraries. In one embodiment, the compounds attached to a solid support are polymers or copolymers, such as polymeric phenolic compounds.

The invention provides a method for producing a combinatorial library using in situ polymerization comprising
providing a functionalized solid support and
enzymatically synthesizing a plurality of compounds, each of the plurality of compounds being attached to a functional group on the solid support.

In a particularly preferred embodiment the solid support has a plurality of totally independent reaction sites arranged in addressable locations. The locations can be arranged in two dimensional arrays, three dimensional arrays, or other matrix formats. The number of locations can range from several to hundreds of thousands or more. In one embodiment, the surface of the solid support is saturated with the compounds.

The solid support can be biological, non-biological, organic, inorganic, or a combination of any of these. The solid support can exist as particles, strands, precipitates, gels, sheets, tubing, spheres, containers, capillaries, pads, slices, films, plates, slides, etc. In the preferred embodiment the solid support is substantially flat. Alternatively, the support surface configuartion can contain, for example, raised or depressed regions or wells that can serve as reaction sites. The material can be opaque or substantially clear. The material of the solid support can be selected from the group of polystyrene cross-linked with divinylbenzene, polyethylene glycol-polystyrene block copolymer, polyamides, polyacrylamide, polymethacrylamide, glass, quartz, cellulose and plastic. Other suitable solid support materials will be apparent to those skilled in the art. Preferably, the surface of the solid support will contain or can be modified to contain reactive chemical groups, such as nnucleophilic groups, carboxyl, amino, hydroxyl, thiol, or the like. More preferably, the surface will have Si—OH functionalities. In a particularly preferred embodiment, the material of the solid support is glass.

The solid support is then reacted with a first monomeric unit of the nascent polymer or copolymer, referred herein as the "seed monomer". The seed monomer can react directly with the surface functionalities or indirectly to the derivatized solid support thus functionalizing the solid support. A seed monomer of the present invention can be any phenol suitable for oxidative phenolic coupling. In one embodiment, a seed monomer has the structure of wherein $R_1$, $R_2$, and $R_3$ are independently selected from a group consisting of a halogen, —R°, —OH, —OR°, —O(haloalkyl), —SH, —SR°, phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R°, —CO$_2$R°, —C(O)R°, —C(O)N(R°)$_2$, —OC(O) R°, —OC(O)N(R°)$_2$, —S(O)$_2$R°, —SO$_2$N(R')$_2$, —S(O)R°, —NR'SO$_2$N(R')$_2$, —NR'SO$_2$R°, —C(=S)N(R')$_2$, —(CH$_2$)$_y$N(R')$_2$, —C(=NH)—N(R')$_2$, haloalkyl, —V—R°, —V—OH, —V—OR°, —V—SH, —V—SR°, —V—NO$_2$, —V—CN, —V—N(R')$_2$, —V—NR'CO$_2$R°, —V—NR'C(O)R°, —V—NR'NR'C(O)R°, —V—N(R')C(O)N(R')$_2$, —V—NR'NR'C(O)N(R')$_2$, —V—NR'NR'CO$_2$R°, —V—C(O)C(O)R°, —V—C(O)CH$_2$C(O)R°, —V—CO$_2$R°, —V—C(O)R°, —V—C(O)N(R°)$_2$, —V—OC(O)R°, —V—OC(O)N(R°)$_2$, —V—S(O)$_2$R°, —V—SO$_2$N(R')$_2$, —V—S(O)R°, —V—NR'SO$_2$N(R')$_2$, —V—NR'SO$_2$R°, —V—C(=S)N(R')$_2$, —V—(CH$_2$)$_y$N(R')$_2$, or —V—C(=NH)—N(R')$_2$;

each R° is independently hydrogen, saturated or unsaturated, substituted or unsubstituted alkyl group or an aromatic group;

each R' is independently R°, —CO$_2$R°, —SO$_2$R° or —C(O)R°;

V is a C1–C6 alkylene group.

In a one particularly preferred embodiment, the seed monomer is p-hydroxyphenylacetic acid or homologs thereof. In another particularly preferred embodiment, the seed monomer is 1,4-hydroquinone.

The solid support can be derivatized with a reagent that, prior to attachment to the solid support, has a reactive site at one end and a polymer synthesis initiation site at the other end. For example, groups appropriate for attachment to glass surface would include trichlorosilyl and trialkoxysilyl functional groups. Groups appropriate to serve as polymer synthesis initiation sites would include amine, hydroxyl, thiol, carboxylic acid, ester, amide, epoxide, isocyanate, and isothiocyanate. Preferred derivatization reagents include aminoalkyltrialkoxysilanes, hydroxyalkyltrichlorosilanes, carboxyalkyltrialkoxysilanes, and epoxyalkyltrialkoxylsilanes. In a particularly preferred embodiment, the derivatizing reagent is 3-aminopropyltriethoxysilane.

The derivatized solid support can be further contacted by a linking molecule, such molecule having at least two reactive chemical groups selected from the group of alkanoyl halides, nitrites, esters, anhydrides, thioesters, and α,β-unsaturated carbonyls. The linking molecules used in the present invention are preferably of sufficient length to permit any polymers synthesized thereon to interact freely with molecules exposed to the polymers. The linking molecules can be about 3 to about 50 or more atoms long. Other suitable linking molecules will be apparent to the one skilled in the art and can include aryl acetylene, ethylene glycol oligomers containing about 2–14 monomer units, diamines, diacids, amino acids, peptides, polynucleotides, and combinations thereof. In a particularly preferred embodiment, the linker molecule has a structure of where n is an integer of about 2.

The solid support can then be subjected to a method for in situ polymerization, preferably an enzymatic synthesis, of a library of the present invention comprising the steps of:

(a) preparing a mixture of reagents comprising at least one monomer, optionally, a wetting agent, and at least one enzyme; and

(b) contacting the functionalized solid support with said mixture allowing for sufficient time to react thereby obtaining oligomers, polymers or copolymers attached to the solid support; and (c) removing the unreacted reagents off the solid support with the pendant oligomers, polymers and copolymers.

Preferably, the methods of the present invention are directed to enzymatic synthesis of libraries of phenolic polymers and copolymers effected by the enzymes capable of catalyzing oxidative coupling. Enzymes that catalyze these reactions can include peroxidases and laccases. Peroxidases are readily available from a variety of sources, both natural and recombinant and include soybean peroxidase, horseradish peroxidase, chloroperoxidase, and mammalian myeloperoxidase. In a particularly preferred embodiment the enzyme is soybean peroxidase. According to the present invention, the functionalized solid support is contacted by a mixture of reagents that comprises at least one enzyme and at least one type of a monomer thereby resulting in elongation of the nascent polymer or copolymer attached to the solid support. More than one distinct monomer can be used, thereby resulting in combinatorial incorporation of the monomers present in the mixture into the nascent copolymer chain. More than one distinct enzyme can be used thereby resulting in variability in both sequence of the nascent polymer or copolymer chain and regio- and stereospecificity of consecutive additions to the nascent chain. Enzymatic catalysis and monomer selection can be used to obtain substantially linear as well as substantially dendritic polymers or copolymers. Steps (a), (b), and, optionally (c) above can be repeated a specified number of times and specified compositions of the reagent mixtures can be used to control length, composition, and topology of the nascent polymer or copolymer chain. In the preferred embodiment, a wetting agent is added to the mixture of reagents to counteract the growing hydrophobicity of the nascent polyphenolic chain. Any of the widely available wetting agents can be used, such as for example Tween 20 or Triton X100. One can also use a suitable organic solvent, such as dimethylformamide or DMSO, for example.

In one embodiment, the monomer has a structure:

wherein $R_1$, $R_2$, and $R_3$ are independently selected from a group consisting of a halogen, —$R^o$, —OH, —$OR^o$, —O(haloalkyl), —SH, —$SR^o$, phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —N(R')$_2$, —NR'$CO_2R^o$, —NR'C(O)$R^o$, —NR'NR'C(O)$R^o$, —N(R')C(O)N(R')$_2$, —NR'NR'C(O)N(R')$_2$, —NR'NR'$CO_2R^o$, —C(O)C(O)$R^o$, —C(O)$CH_2$C(O)$R^o$, —$CO_2R^o$, —C(O)$R^o$, —C(O)N($R^o$)$_2$, —OC(O) $R^o$, —OC(O)N(R')$_2$, —S(O)$_2R^o$, —$SO_2$N(R')$_2$, —S(O)$R^o$, —NR'$SO_2$N(R')$_2$, —NR'$SO_2R^o$, —C(=S)N(R')$_2$, —(CH$_2$)$_y$N(R')$_2$, —C(=NH)—N(R')$_2$, haloalkyl, —V—$R^o$, —V—OH, —V—$OR^o$, —V—SH, —V—$SR^o$, —V—$NO_2$, —V—CN, —V—N(R')$_2$, —V—NR'$CO_2R^o$, —V—NR'C (O)$R^o$, —V—NR'NR'C(O)$R^o$, —V—N(R')C(O)N(R')$_2$, —V—NR'NR'C(O)N(R')$_2$, —V—NR'NR'$CO_2R^o$, —V—C (O)C(O)$R^o$, —V—C(O)$CH_2$C(O)$R^o$, —V—$CO_2R^o$, —V—C(O)$R^o$, —V—C(O)N(R')$_2$, —V—OC(O)$R^o$, —V—OC(O)N($R^o$)$_2$, —V—S(O)$_2R^o$, —V—$SO_2$N(R')$_2$, —V—S(O)$R^o$, —V—NR'$SO_2$N(R')$_2$, —V—NR'$SO_2R^o$, —V—C(=S)N(R')$_2$, —V—(CH$_2$)$_y$N(R')$_2$, or —V—C(=NH)—N(R')$_2$;

each $R^o$ is independently hydrogen, saturated or unsaturated, substituted or unsubstituted alkyl group or an aromatic group;

each R' is independently $R^o$, —$CO_2R^o$, —$SO_2R^o$ or —C(O) $R^o$;

V is a C1–C6 alkylene group, thereby resulting in a repeat unit:

In a preferred embodiment, a monomer of the mixture of reagents has a structure:

thereby resulting in a repeat unit

In another embodiment, a monomer of the mixture of reagents has a structure:

wherein $R_1$, $R_2$, $R_3$, and $R_4$ are independently selected from a group consisting of a halogen, —$R^o$, —OH, —$OR^o$, —O(haloalkyl), —SH, —$SR^o$, phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —$N(R')_2$, —$NR'CO_2R^o$, —$NR'C(O)R^o$, —$NR'NR'C(O)R^o$, —$N(R')C(O)N(R')_2$, —$NR'NR'C(O)N(R')_2$, —$NR'NR'CO_2R^o$, —$C(O)C(O)R^o$, —$C(O)CH_2C(O)R^o$, —$CO_2R^o$, —$C(O)R^o$, —$C(O)N(R')_2$, —$OC(O)R^o$, —$OC(O)N(R^o)_2$, —$S(O)_2R^o$, —$SO_2N(R')_2$, —$S(O)R^o$, —$NR'SO_2N(R')_2$, —$NR'SO_2R^o$, —$C(=S)N(R')_2$, —$(CH_2)_yN(R')_2$, —$C(=NH)—N(R')_2$, haloalkyl, —V—$R^o$, —V—OH, —V—$OR^o$, —V—SH, —V—$SR^o$, —V—$NO_2$, —V—CN, —V—$N(R')_2$, —V—$NR'CO_2R^o$, —V—$NR'C(O)R^o$, —V—$NR'NR'C(O)R^o$, —V—$N(R')C(O)N(R')_2$, —V—$NR'NR'C(O)N(R')_2$, —V—$NR'NR'CO_2R^o$, —V—$C(O)C(O)R^o$, —V—$C(O)CH_2C(O)R^o$, —V—$CO_2R^o$, —V—$C(O)R^o$, —V—$C(O)N(R^o)_2$, —V—$OC(O)R^o$, —V—$OC(O)N(R^o)_2$, —V—$S(O)_2R^o$, —V—$SO_2N(R')_2$, —V—$S(O)R^o$, —V—$NR'SO_2N(R')_2$, —V—$NR'SO_2R^o$, —V—$C(=S)N(R')_2$, —V—$(CH_2)_yN(R')_2$, or —V—$C(=NH)—N(R')_2$;

each $R^o$ is independently hydrogen, saturated or unsaturated, substituted or unsubstituted alkyl group or an aromatic group;

each R' is independently $R^o$, —$CO_2R^o$, —$SO_2R^o$ or —$C(O)R^o$;

V is a C1–C6 alkylene group, thereby resulting in a repeat unit

In a preferred embodiment, the monomer has a structure:

thereby resulting in a repeat unit

In yet another embodiment, the monomer has a structure:

wherein $R_1$ is selected from a group consisting of a halogen, —$R^o$, —OH, —$OR^o$, —O(haloalkyl), —SH, —$SR^o$, phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —$N(R')_2$, —$NR'CO_2R^o$, —$NR'C(O)R^o$, —$NR'NR'C(O)R^o$, —$N(R')C(O)N(R')_2$, —$NR'NR'C(O)N(R')_2$, —$NR'NR'CO_2R_o$, —$C(O)C(O)R^o$, —$C(O)CH_2C(O)R^o$, —$CO_2R^o$, —$C(O)R^o$, —$C(O)N(R')_2$, —$OC(O)R^o$, —$OC(O)N(R^o)_2$, —$S(O)_2R^o$, —$SO_2N(R')_2$, —$S(O)R^o$, —$NR'SO_2N(R')_2$, —$NR'SO_2R^o$, —$C(=S)N(R')_2$, —$(CH_2)_yN(R')_2$, —$C(=NH)—N(R')_2$, haloalkyl, —V—$R^o$, —V—OH, —V—$OR^o$, —V—SH, —V—$SR^o$, —V—$NO_2$, —V—CN, —V—$N(R')_2$, —V—$NR'CO_2R^o$, —V—$NR'C(O)R^o$, —V—$NR'NR'C(O)R^o$, —V—$N(R')C(O)N(R')_2$, —V—$NR'NR'C(O)N(R')_2$, —V—$NR'NR'CO_2R^o$, —V—$C(O)C(O)R^o$, —V—$C(O)CH_2C(O)R^o$, —V—$CO_2R^o$, —V—$C(O)R^o$, —V—$C(O)N(R^o)_2$, —V—$OC(O)R^o$, —V—$OC(O)N(R^o)_2$, —V—$S(O)_2R^o$, —V—$SO_2N(R')_2$, —V—$S(O)R^o$, —V—$NR'SO_2N(R')_2$, —V—$NR'SO_2R^o$, —V—$C(=S)N(R')_2$, —V—$(CH_2)_yN(R')_2$, or —V—$C(=NH)—N(R')_2$;

each $R^o$ is independently hydrogen, saturated or unsaturated, substituted or unsubstituted alkyl group or an aromatic group;

each R' is independently $R^o$, —$CO_2R^o$, —$SO_2R'$ or —$C(O)R^o$;

V is a C1–C6 alkylene group, thereby resulting in a repeat unit

In a preferred embodiment, the monomer has a structure:

thereby resulting in a repeat unit

The present invention also relates to high-throughput enzymatic synthesis of phenolic polymers and copolymers on solid support. The synthesis of compounds of the present invention can proceed in parallel at large number of addressable reaction sites. Generally known techniques include, but are not limited to, "light-directed" methods, "flow-channel" methods, "spotting" methods, and "pin"-based methods.

"Light-directed" methods involve activating predefined regions of a solid support and then contacting the solid support with a predefined mixture of reagents containing a desired monomer. The predefined regions can be activated by a light source, typically shown through a mask. Other regions of the solid support remain inactive because they are blocked by the mask from illumination and remain chemically protected. Thus a light pattern defines which regions of the solid support react with a given monomer. Repeatedly activating different sets of predefined regions and contacting these regions with different monomers results in a diverse array of polymers.

In "flow-channel" methods, the flow channels are formed on the surface of a solid support through which appropriate reagents flow or into which appropriate reagents are placed. Channels are selectively blocked thereby allowing a mixture of reagents to contact predetermined regions of the solid support. Blocking of the channels is achieved, for example, by applying hydrophobic or hydrphilic coating onto predetermined regions of the solid support. The diversity is generated by repeatedly contacting predetermined regions of the solid support by predetermined monomers using selective flow of the mixture of reagents.

The "spotting" methods are implemented by directly depositing relatively small aliquots of predetermine mixtures of reagents onto predetermined regions of a solid support. In some steps the entire surface of the solid support can be sprayed or otherwise coated with a mixture of reagents. In a preferred embodiment, a dispenser moves from region to region. The diversity is achieved by delivering predetermined mixtures of reagents to a predetermined regions of the solid support.

The "pin"-based methods utilize solid supports having a plurality of pins or other extensions. The pins are each inserted simultaneously into a tray having a plurality of containers with, possibly distinct, reaction mixtures and allowing the chemical reactions to proceed. The diversity is generated by repeatedly inserting the pins into containers with distinct reaction mixtures.

One skilled in the art will recognize that there are alternative methods for generating a diverse library of the present invention using the means described herein and that additional steps, such as removing the unreacted reagents off the solid support with the pendant polymers and copolymers.

The reagents necessary for each step can be delivered by using a variety of means. For example, a syringe pump, a pipettor, including a micropipettor or multichannel pipettor can be used, and/or an inkjet printer can be used. Reagents that can be delivered to the reaction sites on the solid support can include solid support derivatizing agents, bifunctional (linking) reagents, seed monomers, reaction mixtures comprising at least one monomer, an optional wetting agent, and at least one enzyme. Optionally, necessary solvents and washing agents, including water, can be delivered to or removed from the reaction sites using the above described embodiments.

In a preferred embodiment, reagents are delivered to the reaction sites using robotic dispensers. A typical dispenser includes a micropipettor to deliver a reagent or a mixture of reagents to the solid support and a robotic system to control the position of the micropipettor, with respect to the sold support, or an inkjet printer. In other embodiments, the dispenser includes a series of tubes, a manifold, an array of pipettes, or the like so that various reagents can be delivered to the reaction site simultaneously.

A useful tool in conducting high-throughout parallel synthesis is a robotic microarray spotter. Of the many commercial spotters available, there are, for example, contact pin spotters such as the GeneTAC $G^3$ (Genomic Solutions, Lansing, Mich.) and piezoelectric (inkjet mechanism) spotters such as the NANO-PLOTTER NP1.2™ (GeSiM mbH, Grosserkmansdorf, Germany).

The libraries of compounds synthesized according to the methods of the present invention can be used for identification of molecules with biological, enzymatic, or medicinal activity. Such activities can include binding, stimulation, inhibition, toxicity, cytotoxicity, taste, enzyme activity, enzyme inhibition, and chemical and physical properties of interest.

The present invention allows identification of synthetic compound that bind to receptor molecules. As used herein, the term "receptor molecule" refers to any molecule which binds to a ligand. Receptor molecules can be biological macromolecules such as antibodies, enzymes, nucleic acids, cytosolic and surface proteins, or smaller molecules such as certain carbohydrates, lipids, organic compounds serving as drugs, metals, etc. The synthetic compound in libraries of the invention can potentially interact with many different receptor molecules. By identifying the particular ligand species to which a specific receptor molecule binds, it becomes possible to physically isolate the ligand species of interest. In the method of the invention, an acceptor molecule of interest is introduced to the library where it will recognize and bind to one or more ligand species within the library. Each ligand species to which the receptor molecule binds will be found on an addressable reaction site on a solid support so that the support, and thus the ligand, can be readily identified and isolated. In addition to using soluble receptor molecules, in another embodiment, it is possible to detect ligands that bind to cell surface receptors using intact cells. The use of intact cells is preferred for use with receptors that are multi-subunit or labile or with receptors that require the lipid domain of the cell membrane to be functional. The cells used in this technique can be either live or fixed cells. The cells can be incubated with the library and bind to certain compounds in the library identifiable by their addressable locations. As an alternative to whole cell assays for membrane bound receptors or receptors that require the lipid domain of the cell membrane to be functional, the receptor molecules can be reconstituted into liposomes where a reporting group or enzyme can be attached.

In the preferred embodiment, the receptor molecule can be directly labeled. In another embodiment, a labeled secondary reagent can be used to detect binding of a receptor molecule to a solid support with a pendant ligand of interest. Binding can be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different receptor molecules of interest, can be used. Cross-reactive and singly-reactive ligands can be identified with a two-color assay.

In another embodiment, the ligand or ligands with the greatest binding affinity can be identified by progressively diluting the receptor molecule of interest until binding to only a few solid support locations is detected. Alternatively, stringency of the binding with the acceptor molecule, can be increased. One of ordinary skill would understand that stringency of binding can be increased by such means as increasing solution ionic strength; increasing the concentration of denaturing compounds such as urea; increasing or decreasing assay solution pH; inclusion of a defined concentration of known competitor into the reaction mixture; and lowering the receptor concentration. Other means of changing solution components to change binding interactions are well known in the art.

In another embodiment, ligands that demonstrate low affinity binding can be of interest. These can be selected by first removing high affinity ligands and then detecting binding under low stringency or less dilute conditions.

The instant invention further provides assays for biological activity of a ligand-candidate from a library. The biological activities that can be assayed include toxicity and killing, stimulation and growth promotion, signal transduction, biochemical and biophysical changes, and physiological change. It can be necessary to remove the compounds of the libraries from a solid support. This can be achieved by selectively cleaving a compound of interest off the solid support using any of means of reagent delivery described above. Examples of cleaving agents include, but are not limited to, UV light, acid, base, enzyme, or catalyst. In practice, one of ordinary skill would be able to readily determine appropriate cleavage conditions. Biological assays with both cleaved-off synthetic compound and compound attached to the solid support are envisioned by the present invention. In one embodiment, synthetic compounds are added to a cell culture or cell extract. In another embodiment, aliquots of cell culture or cell extract are delivered to the addressably located synthetic compounds.

The present invention further encompasses libraries of molecules that can inhibit enzyme reactions. Thus, the invention also provides methods to be used to assay inhibition of enzyme activity. Enzyme inhibitory activity can be detected with a cleavead-off as well as attached synthetic compound. In one embodiment, the enzyme substrate is chromogenic, and a colored product is formed. Thus, presence of an enzyme inhibitor would yield a zone of no color. In another embodiment the enzyme or parts thereof are labeled by a tracer capable of generating a detectable signal, such as, for example, fluorescent marker. The presence of a signal will indicate binding, including formation of a covalent and non-covalent complexes and possible inactivation of an enzyme of interest, to one or more synthetic compounds of the present invention. An enzyme of interest or a part thereof can form a covalent bond with a compound of the library, thereby forming a complex that, following cleaving of said complex off the solid support, can be detected by a variety of physico-chemical methods known in the art, such as, for example, MALDI-ToF. For example, and not by way of limitation, a number of the molecules that can be synthesized according to the methods of the present invention formed a covalent bond with a Cysteine residue on a synthetic peptide derived from p47phox subunit of endothelial NADPH oxidase. (See Example 3). Molecules synthesized according to the methods of the present invention can bind to hydrophobic, particularly Proline-rich, peptides thereby forming non-covalent complexes with, for example, peptides of the NADPH oxidase assembly.

Following identification of a compound or compounds of the libraries of the present invention in the screening assays described above, the structure of a the desired polymer or copolymer is known due to it being addressably attached to a solid support. The structure can be confirmed, following cleavage off the support, by any of the physico-chemical methods known in the art including, but not limited to gas chromatography, liquid chromatography, and, preferably, MALDI-ToF.

Synthetic compounds and libraries of compounds synthesized or screened according to the methods of the present invention can be used in a wide variety of fields. A molecule that has been identified through library screening can be used in treatment or diagnosis of disease. The molecule identified through screening alone can provide a diagnostic or therapeutic agent, or can be incorporated into a larger molecule. A molecule comprising a structure with biological or binding activity can be termed an "effector molecule." The method described herein not only provides a new tool to search for specific ligands of potential diagnostic or therapeutic value, but also provides important information on a series of ligands of potentially vastly different structure which nonetheless are able to interact with the same receptor molecule. Integrating such information with molecular modeling and modem computational techniques is likely to provide new fundamental understanding of ligand-receptor interactions. The therapeutic agents of the invention comprise effector molecules that will bind to the biologically active site of cytokines, growth factors, or hormonal agents and thereby enhance or neutralize their action, and that will block or enhance transcription and/or translation. The therapeutic agents of the invention include, for example, effector molecules that bind to a receptor of pharmacologic interest such as growth factor receptors, neurotransmitter receptors, or hormone receptors. These effector molecules can be used as either agonists or antagonists of the action of the natural receptor ligand. Another application of effector molecules that bind to receptors would be to use the binding to block the attachment of viruses or microbes that gain access to a cell by attaching to a normal cellular receptor and being internalized. Examples of this phenomenon include the binding of the human immunodeficiency virus to the CD4 receptor, and of the herpes simplex virus to the fibroblast growth factor receptor. Effector molecules that occupy the receptor could be used as pharmacologic agents to block viral infection of target cells. Parasite invasion of cells could be similarly inhibited, after suitable effector molecules were identified according to this invention. In one embodiment, the receptor molecule of interest is a receptor or antigen found on the surface of a tumor cell, animal parasite, or microbe, e.g., bacterium, virus, unicellular parasite, unicellular pathogen, fungus or mold. In another embodiment, the targeted entity is an intracellular receptor. In general, the present invention envisions providing methods to identify molecules for therapy of diseases or illnesses such as are listed in the Product Category Index of The Physicians Desk Reference (PDR, 1993, 47th Edition, Medical Economics Data: Oradell, N.J., pp. 201–202). For example, an effector molecule with anti-cancer, antiparasite, anticoagulant, anticoagulant antagonist, antidiabetic agent, anticonvulsant, antidepressant, antidiarrheal, antidote, antigonadotropin, antihistamine, antihypertensive, antuinflammatory, antinauseant, antimigraine, antiparkinsonism, antiplatelet, antipruritic, antipsychotic, antipyretic, antitoxin (e.g., antivenin), bronchial dilator, vasodilator, chelating agent, contraceptive, muscle relaxant, antiglaucomatous agent, or sedative activity can be identified. The therapeutic agents and diagnostic agents of the instant invention can be used for the treatment and/or diagnosis of animals, and more preferably, mammals including humans, dogs, cats, horses, cows, pigs, guinea pigs, mice and rats. Therapeutic or diagnostic agents can also be used to treat and/or diagnose plant diseases. The diseases and conditions amenable to therapy or diagnosis with molecules discovered according to the present invention are as varied and wide-ranging as the permutations of structures in a library.

For example, and not by way of limitation, a number of the molecules that can be synthesized according to the methods of the present invention formed a covalent bond with a Cysteine residue on a synthetic peptide derived from p47phox subunit of endothelial NADPH oxidase. (See Example 3). Thereby, the oligophenols of the present invention has shown significance as potential inhibitors of NADPH oxidase assembly. NADPH oxidase is involved in generation of superoxide that then forms several Reactive Oxygen Species (ROS). Inhibiting the source of superoxide, rather than scavenging ROS, is a better strategy for combating diseases stemming form vascular hyperpermeability. ROS also lead to formation of plaques on the inner surface of blood vessels resulting in partial or complete vessel occlusion. Among the diseases that are linked to NADPH oxidase and therefore can treated with the compounds of the present invention or their derivatives are atherosclerosis, hypertension, ischemia, several liver and kidney diseases, diabetic retinopathy and arthritis. HfV progression and oncogenic transformations are also linked to NADPH oxidase activity.

Thus, the invention includes the oligophenols useful in the treatment of NADPH oxidase mediated disease, as taught in U.S. Pat. No. 5,902,831 by Holland et al. the content of which is incorportaed herein by reference.

While this invention has been particularly shown and described with references to preferred embodiments thereof, it will be understood by those skilled in the art that various changes in form and details can be made therein without departing from the scope of the invention encompassed by the appended claims.

EXEMPLIFICATION

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 1:
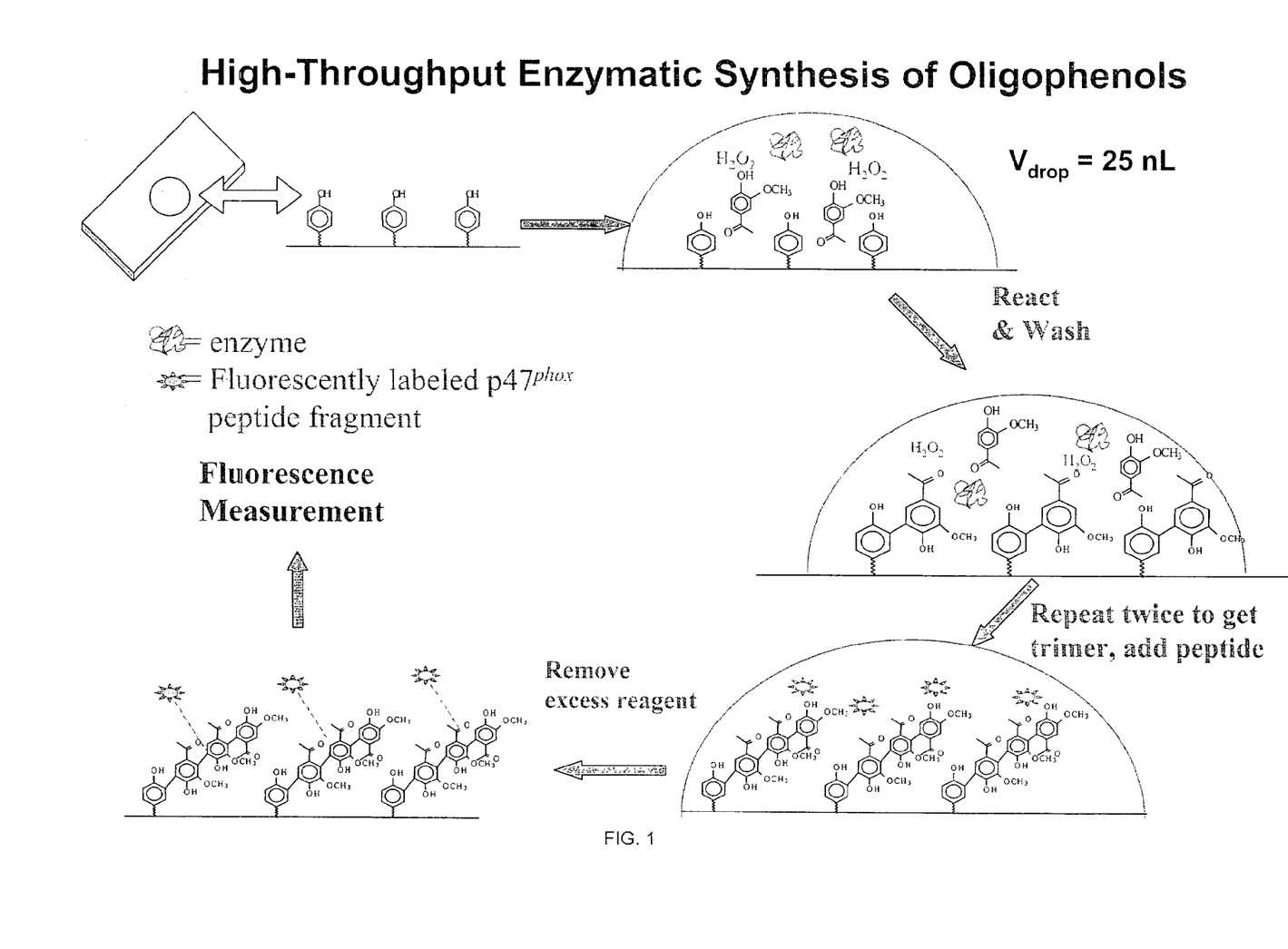

Referring to FIG. 1, a solid support with addressable locations is functionalized and a seed monomer, exemplified by a phenol moiety, is covalently attached to said solid support. A small aliquot of a mixture of reagents is then deposited onto each addressable location, said mixture containing an enzyme, a monomer, exemplified by apocynin, and a polymerization initiator, exemplified by hydrogen peroxide. The first step of the library growth is allowed to proceed, whereby apocynin is covalently attached to the seed monomer via oxidative coupling. Each addressable location is then washed and a new aliquot is added, possibly containing a different monomer and/or enzyme. The whole process is repeated the desirable number of times. When the library is deemed complete, it is screened by a ligand of interest, exemplified by a peptide $p47^{phox}$, a subunit of the endothelial NADPH oxidase. The ligand is carrying a signal-generating tracer, exemplified by a flourescent tag. An addressable location that has a molecule capable of binding the ligand attached to solid support is then detected by measuring fluorescence. The identity of the molecule capable of binding the ligand is ascertained from the address of the location on the solid support to which said molecule is attached.

EXAMPLE 1

Solid Phase Synthesis of Oligophenols

The process of growing oligophenols is achieved through the following steps:

1. Acid Wash

Standard glass slides (75 mm×25 mm) are acid washed first in a 1:1 Methanol:HCl solution and then in concentrated $H_2SO_4$ to expose the silanol groups. Each of these steps is 2–6 h long, and is followed by a wash in deionized water and drying under nitrogen.

2. APTES Treatment and the Deposition of Seed Phenol Monomer

Figure 2A:
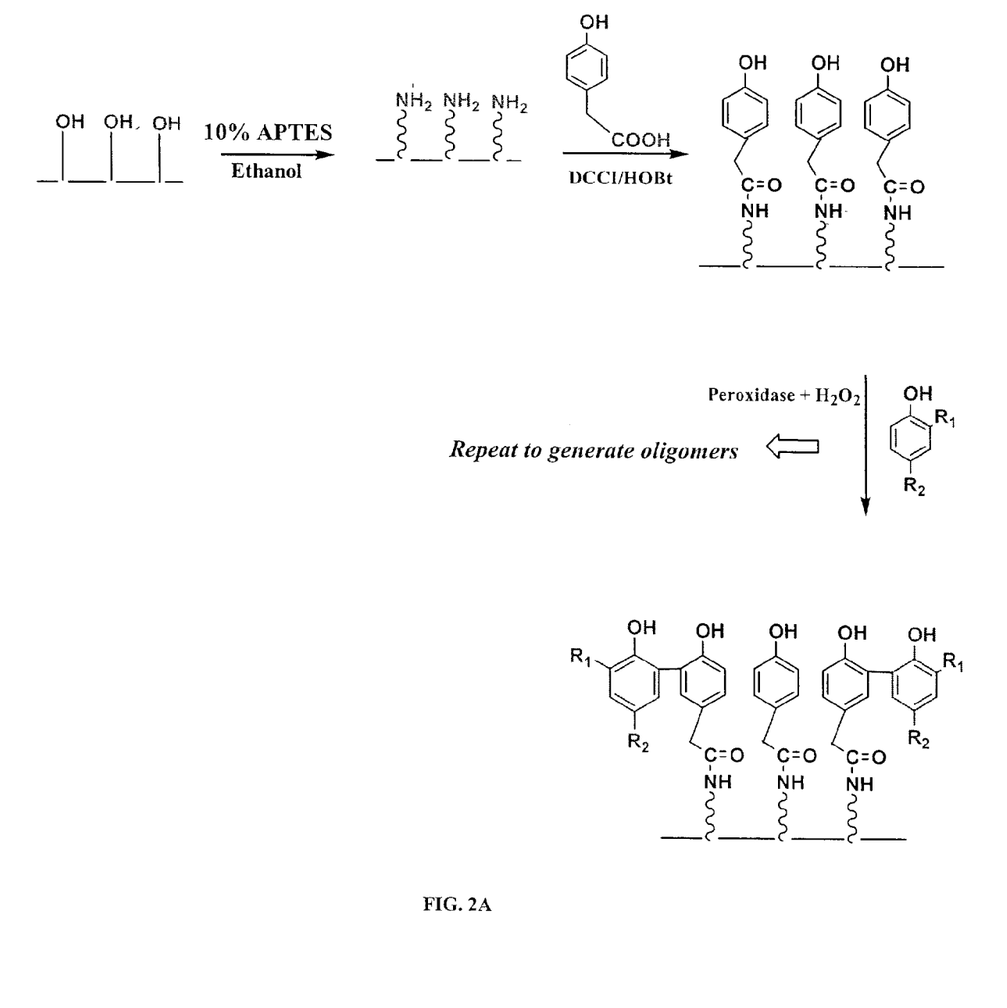
Figure 2B:
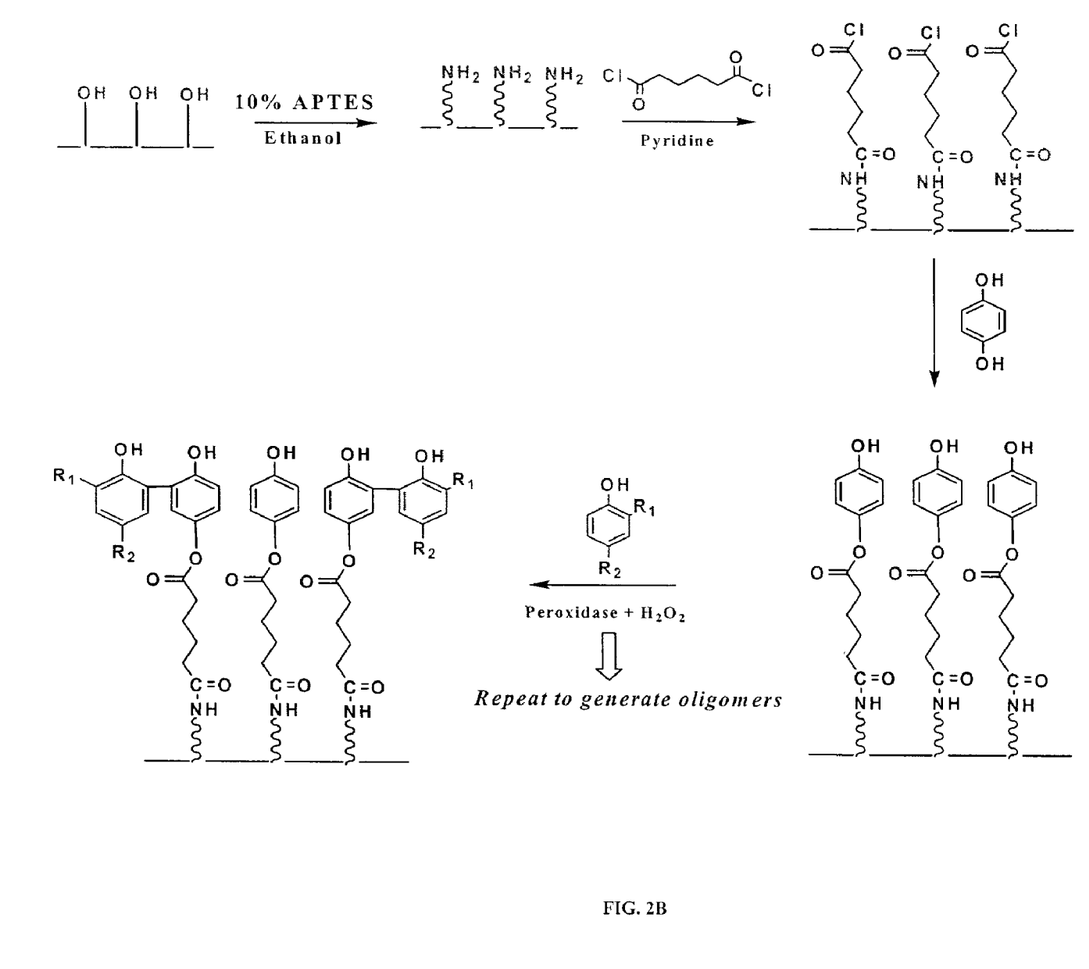

Referring to FIGS. 2A and 2B, the functional groups available on the solid support, exemplified by the hydroxyl moieties, are converted into desirable moieties, exemplified by amines, by 3-aminopropyl-triethoxysilane (APTES). Optionally, the solid support is further derivatized by reacting amino groups with a bifunctional linker molecule, exemplified by 1,6-hexanedioyl chloride (FIG. 2B). Next, the seed monomer, exemplified by hydroquinone, is attached to the functionalized solid support via a covalent ester bond. The synthesis of a library proceeds by adding a mixture of reagents containing an enzyme, a monomer, and a polymerization initiator.

The acid washed slides are exposed to a 10% w/v solution of APTES (3-aminopropyltriethoxysilane) in ethanol for 30 min, washed in ethanol, and dried in an oven at 100° C. for 12 h. This leads to primary amino groups on the glass slide.

Deposition of seed phenol was achieved in one of the following two ways.

(a) p-hydroxyphenylacetic acid (HyPAA) or its homologues can be attached to the glass slide via DCC/HOBt mediated formation of an amide bond with the primary amino groups on the slide (See FIG. 2A for chemistry). A solution of 100 mM each of HyPAA, DCC, and HOBt is prepared in DMF, and 8 slides are immersed in 200 ml of this solution at 60° C., accompanied by gentle shaking. The slides are removed from the reaction mixture at the end of 10 h, washed 3× in DMF, 2× in toluene, air dried and stored until further use. In this case, the seed phenol is attached to the slide via amide bonds.

(b) Hydroquinone is attached by a two-step method involving adipoyl chloride. The adipoyl chloride (10 mM) is first reacted with the primary amino groups on the glass slides in the presence of 10 mM pyridine for 6 h (8 slides in 200 ml total volume). The slides are removed, and washed in 3 times in DMF. Care must be taken to prevent exposure to moisture during this step. Next, the 8 slides are treated with 200 ml of 10 mM hydroquinone also in the presence of 10 mM pyridine in DMF to obtain the seed phenol layer (See FIG. 2B for chemistry). The slides are then washed 3× in DMF and 2× in toluene, air dried and stored until further use. In this case, the seed phenol is attached to the slide through ester linkages.

3. Peroxidase Catalyzed Oligomerization

The seed phenol containing glass slides are treated with 10 mM phenol in the presence of 1–10 µg/ml soybean peroxidase and 0.2–1 mM hydrogen peroxide in 15 ml of 100 mM pH 7 phosphate buffer containing 20–30% v/v DMF. In the case of amide bonded seed phenol, this step can be 0.5–2.0 h long, while in the case of ester linked phenols, the reaction is terminated at the end of 15–30 min. Two controls were performed: one contaning all the reagents except enzyme, the other deficient in $H_2O_2$.

4. Analysis of Peroxidase Reactions

Two types of reactions were performed and analyzed.

(a) Tyramine as substrate: In this case, tyramine is attached using peroxidase catalysis to the seed phenol and the reaction is monitored by measuring the amino-group density at the end of each step using the method of Gaur and Gupta (1989, see FIGS. 3A, 3B, and 3C).

(b) Apocynin as substrate: This reaction was performed only on the ester linked seed phenols and analyzed by cleaving the dimer off the slide using acid (or base) hydrolysis, followed by freeze drying, and finally, Direct-Insertion Mass Spectroscopy, where the solid sample is analyzed in the electron impact mode.

EXAMPLE 2

Quantification of Amino Group Density

Reaction on slides was followed by monitoring the number of amino groups on a slide. Slides were immersed in 15 ml 1 mM sulfo-SDTB in 50 mM sodium bicarbonate and shaken vigorously for 30 min, after which they were removed washed with DI water and air-dried. Upon the addition of 5 ml of perchloric acid, the dimethoxytrityl cation is released, which absorbs at 498 nm. An extinction coefficient of 70,000 $M^{-1}cm^{-1}$ is used to quantify the amino group density on the slides.

Figure 3A:
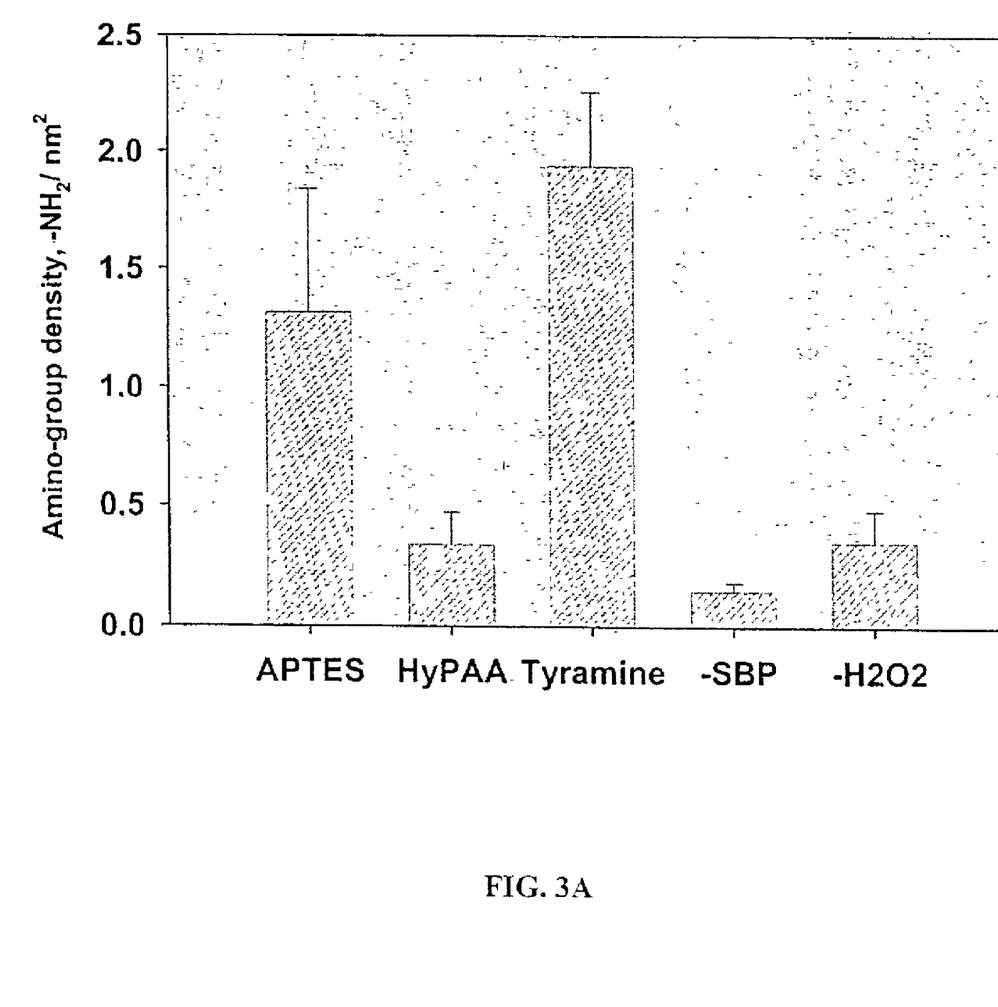
Figure 3B:
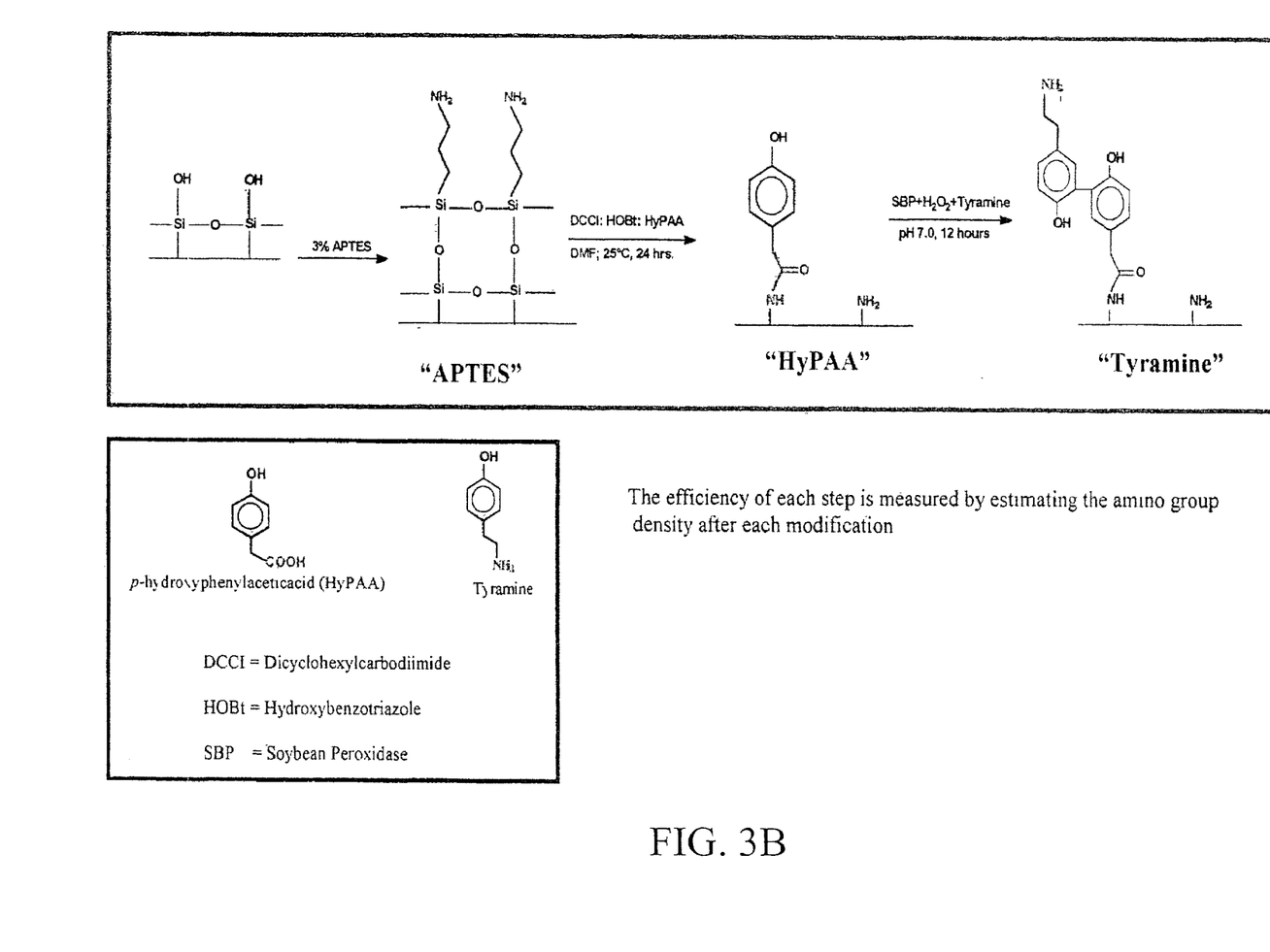
Figure 3C:
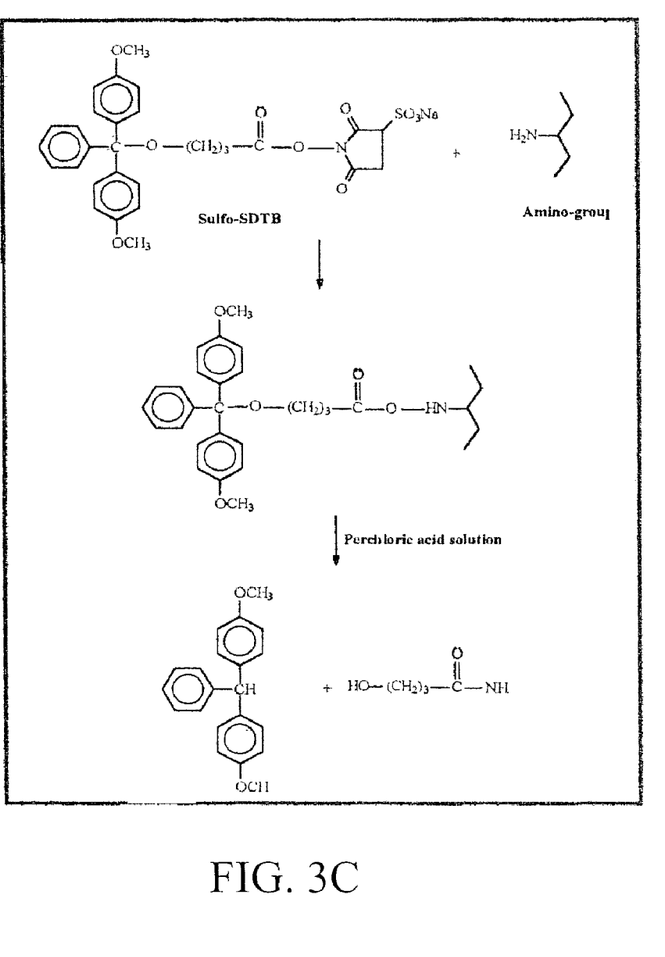

Referring to FIGS. 3A, 3B, and 3C. As depicted in FIG. 3B, the solid support, exemplified by glass surface, is functionalized by APTES, derivatized by the seed monomer (HyPAA) and subjected to enzymatic coupling reaction, wherein the enzyme is the soybean peroxidase and the monomer is the tyramine. Each step of this process is monitored by the method of Gaur and Gupta (1989), illustrated in FIG. 3C. Using the chemical steps shown in FIG. 3C, the amino functionalities are quantitatively detected. The results are shown in FIG. 3A, which clearly indicates that soybean peroxidase is able to catalyze phenolic coupling on solid support. Turning to FIG. 3A, APTES coating efficiency is the average of 10 replicates. The others are averages of 5 replicates. Two controls were performed for the tyramine step: one in which the functionalized solid support was incubated in the presence of all reagents except the enzyme and the other in which peroxide was absent.

EXAMPLE 3

Screening Techniques

1. Synthesis of Oligophenols in Solution

One gram of monomer (apocynin, vanillin, or 0.5 mg each of apocynin and vanillin) is dissolved in 5 ml DMF and transferred to 490 ml of 100 mM phosphate buffer, pH 7. To this mixture, 5 ml of a 1 mg/ml solution of SBP in buffer is added. The reaction is initiated by the addition of $H_2O_2$ in one of two ways: either as a bolus of 100 µl 30% $H_2O_2$ solution (=1.7 mM $H_2O_2$) or 1.5 ml of 30% $H_2O_2$ over 12 h using a syringe pump. The oxidation products precipitate and are removed by centrifugation. The pellet is washed several times in DI water, dried, and stored until further use. Another bolus addition of 100 µl of 30% $HO_2$ is made to the supernatant, and the second reaction products are also removed by centrifugation, washed in DI water, dried, and stored.

2. Reaction of Oligophenols with Cysteine Containing Peptides

Figure 4A:
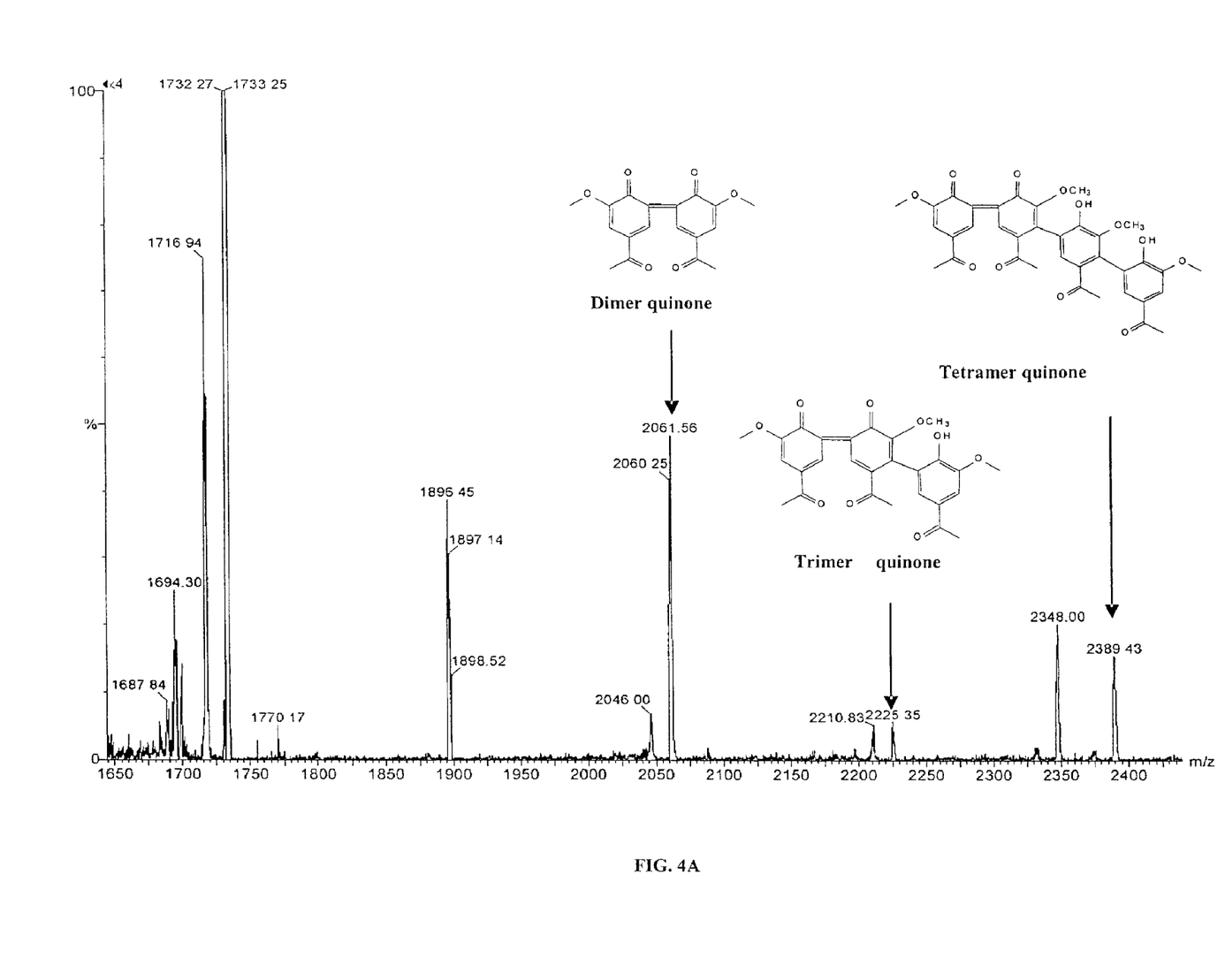
FIGS. 4A, 4B, and 4C show the MALDI-ToF analysis of the products of the reactions of the $p47^{phox}$ with various oligophenols that can be synthesized using the methods of the present invention.
Figure 4B:
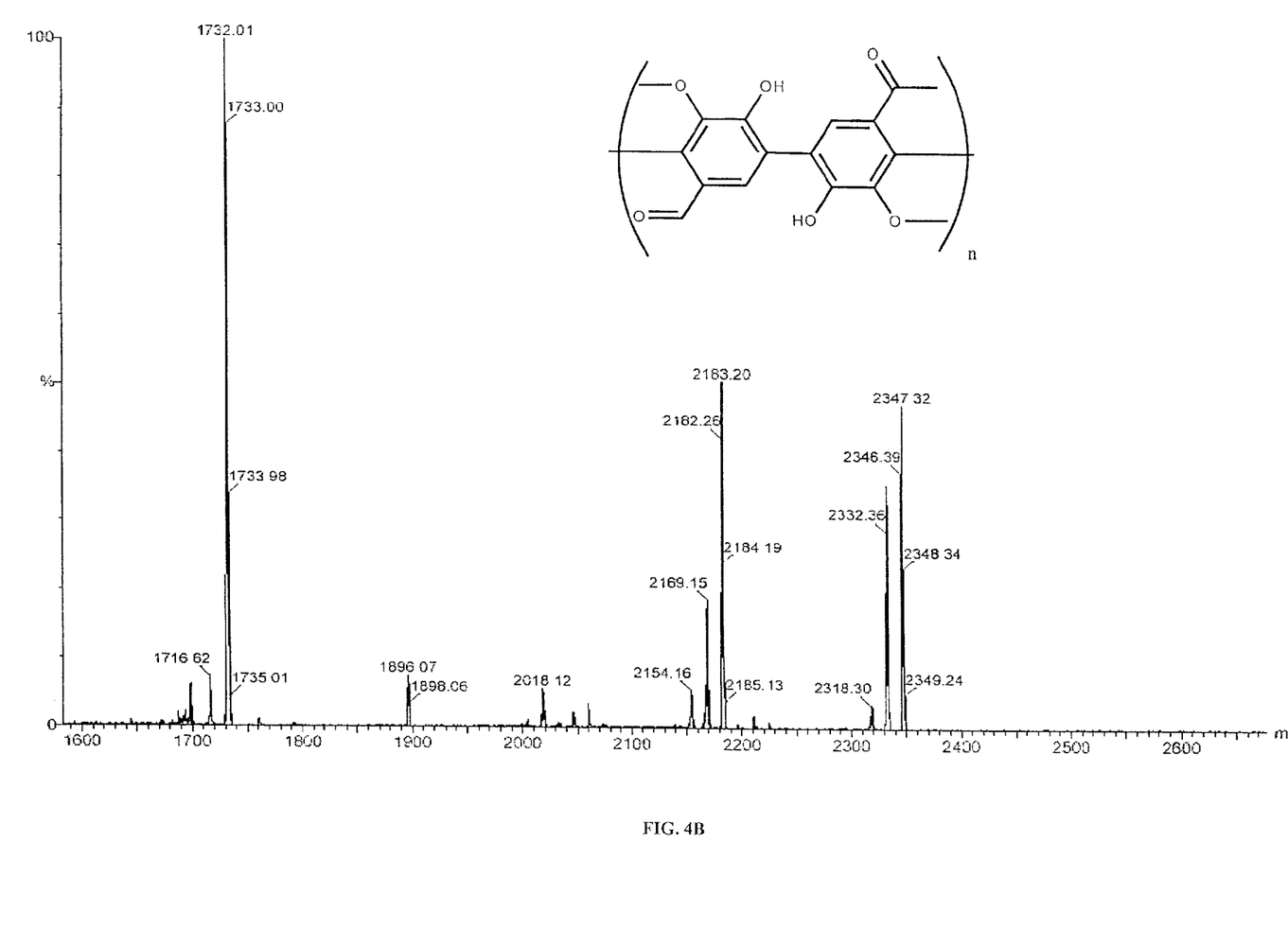
Figure 4C:
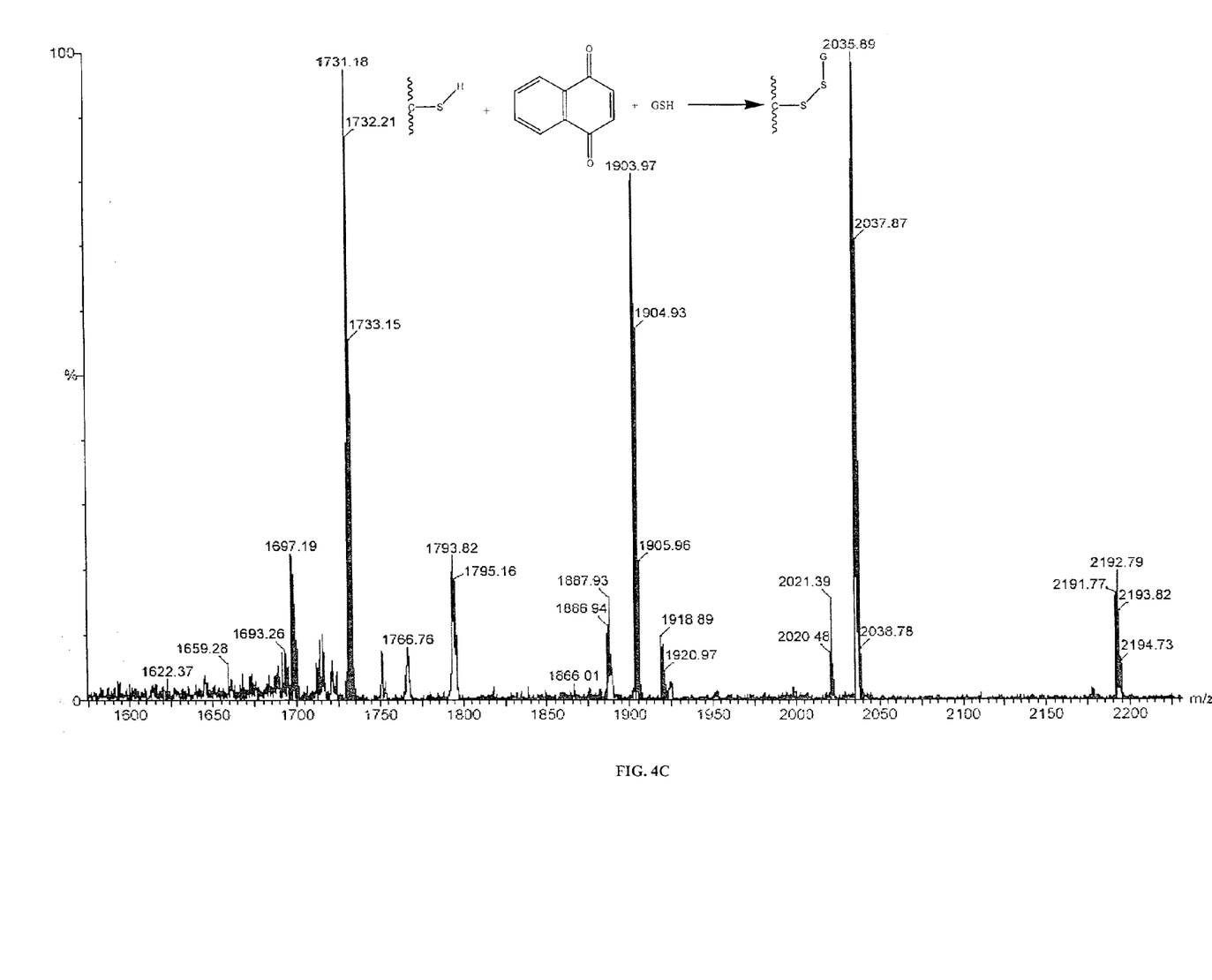

The p47phox subunit of endothelial NADPH oxidase has cysteine containing peptidic regions. One of these peptides was synthesized and employed for this work. The peptide stock is prepared at a concentration of 1 mg/ml in DI water, and the phenol oxidation products are dissolved at a concentration of 10 mg/ml in acetonitrile. For reaction, both components are added to DI water such that their concentration is 0.1 mg/ml. The reaction products are identified using MALDI-ToF (FIGS. 4A, 4B, and 4C). As controls, 1,2-naphthoqionone and 1,4-naphthoqionone were reacted with the peptide. Additionally, these reactions were also performed in the presence of glutathione. Referring to FIGS. 4A, 4B, and 4C. The MALDI-ToF analysis of the products of the reaction of a synthetic peptide derived from p47$^{phox}$ subunit of the endothelial NADPH oxidase with various oligophenols that can be synthesized according to the methods of the present invention are shown. FIG. 4A shows peaks corresponding to the peptide covalently bound to apocynin oxidation products that include dimers, trimers, and tetramers. FIG. 4B shows peaks corresponding to the peptide covalently bound to the products of oxidative coupling of apocynin-vanillin copolymer. FIG. 4C shows the peak corresponding to glutathion-bound peptide. Since the presence of glutathion prevents reaction between the peptide and the products of oxidative peptide coupling, FIG. 4C presents the evidence for covalent nature of the p47$^{phox}$ inactivation and for the role of a Cysteine and its sulfhydryl moiety.

What is claimed is:

1. A combinatorial library comprising a solid support and a plurality of addressable polymeric or copolymeric polyphenolic compounds, wherein the polymer or copolymer comprises a repeat unit having the structure:

and further wherein $R_1$, $R_2$, and $R_3$ are independently selected from a group consisting of a halogen, —R°, —OH, —OR°, —O(haloalkyl), —SH, —SR°, phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)

R°, —C(O)CH₂C(O)R°, —CO₂R°, —C(O)R°, —C(O)N(R°)₂, —OC(O)R°, —OC(O)N(R°)₂, —S(O)₂R°, —SO₂N(R')₂, —S(O)R°, —NR'SO₂N(R')₂, —NR'SO₂R°, —C(=S)N(R')₂, —(CH₂)ᵧN(R')₂, —C(=NH)—N(R')₂, haloalkyl, —V—R°, —V—OH, —V—OR°, —V—SH, —V—SR°, —V—NO₂, —V—CN, —V—N(R')₂, —V—NR'CO₂R°, —V—NR'C(O)R°, —V—NR'NR'C(O)R°, —V—N(R')C(O)N(R')₂, —V—NR'NR'C(O)N(R')₂, —V—NR'NR'CO₂R°, —V—C(O)C(O)R°, —V—C(O)CH₂C(O)R°, —V—CO₂R°, —V—C(O)R°, —V—C(O)N(R°)₂, —V—OC(O)R°, —V—OC(O)N(R°)₂, —V—S(O)₂R°, —V—SO₂N(R')₂, —V—S(O)R°, —V—NR'SO₂N(R')₂, —V—NR'SO₂R°, —V—C(=S)N(R')₂, —V—(CH₂)ᵧN(R')₂, or —V—C(=NH)—N(R')₂;

each R° is independently hydrogen, saturated or unsaturated, substituted or unsubstituted alkyl group or an aromatic group;

each R' is independently R°, —CO₂R°, —SO₂R° or —C(O)R°;

V is a C1–C6 alkylene group, wherein each of the polymeric or copolymeric addressable compounds is attached to said sold support and said attachment is effectuated by a seed monomer.

2. The library of claim 1 wherein the polymer or copolymer comprises a repeat unit having the structure:

3. The library of claim 1, wherein the seed monomer is p-hydroxyphenylacetic acid or a homolog thereof.

4. The library of claim 3, wherein the seed monomer is attached to said solid support by a covalent amide bond and further wherein said amide bond is formed between an amino functionality of said support and a carboxyl group of said seed monomer.

5. The library of claim 1, wherein said seed monomer is 1,4-hydroquinone.

6. The library of claim 5, wherein attaching said seed monomer to said solid support is effected by an adipoyl chloride linker, and further wherein a first carbonyl moiety of said adipoyl chloride linker forms a covalent ester bond with a hydroxyl group of said 1,4-hydroquinone seed monomer and a second carbonyl moiety of said adipoyl chloride linker forms a covalent amide bond with an amino functionality of said solid support.

7. The library of claim 4, wherein the seed monomer is attached to said solid support by a covalent amide bond between an amino functionality of 3-aminopropyltriethoxysilane (APTES) and a carboxyl group of said seed monomer.

8. The library of claim 1 wherein the solid support is glass.

9. A combinatorial library comprising a solid support and a plurality of addressable polymeric or copolymeric polyphenolic compounds, wherein each of the addressable polymeric or copolymeric polyphenolic compounds is attached to said solid support and said attachment is effectuated by, wherein the seed monomer is p-hydroxyphenylacetic acid or a homolog thereof, or 1,4-hydroquinone.

10. The library of claim 9, wherein the seed monomer is attached to said solid support by a covalent amide bond and further wherein said amide bond is formed between an amino functionality of said support and a carboxyl group of said seed monomer.

11. The library of claim 9, wherein attaching said seed monomer to said solid support is effectuated by an adipoyl chloride linker, and further wherein a first carbonyl moiety of said adipoyl chloride linker forms a covalent ester bond with a hydroxyl group of said 1,4hydroquinone seed monomer and a second carbonyl moiety of said adipoyl chloride linker forms a covalent amide bond with an amino functionality of said solid support.

12. The library of claim 10, wherein the seed monomer is attached to said solid support by a covalent amide bond between an amino functionality of 3-aminopropyltriethoxysilane (APTES) and a carboxyl group of said seed monomer.

* * * * *